US009603531B2

(12) United States Patent
Natarajan

(10) Patent No.: US 9,603,531 B2
(45) Date of Patent: *Mar. 28, 2017

(54) IN-PLACE DISPLAY ON SENSORY DATA

(71) Applicant: Indian Institute of Science, Karnataka (IN)

(72) Inventor: Vijay Natarajan, Bangalore (IN)

(73) Assignee: INDIAN INSTITUTE OF SCIENCE, Karnataka (IN)

(*) Notice: Subject to any disclaimer, the term of this patent is extended or adjusted under 35 U.S.C. 154(b) by 583 days.

This patent is subject to a terminal disclaimer.

(21) Appl. No.: 14/152,663

(22) Filed: Jan. 10, 2014

(65) Prior Publication Data
US 2014/0128756 A1 May 8, 2014

Related U.S. Application Data

(63) Continuation of application No. 12/550,199, filed on Aug. 28, 2009, now Pat. No. 8,641,617.

(30) Foreign Application Priority Data

Apr. 2, 2009 (IN) .............................. 766/CHE/2009

(51) Int. Cl.
*A61B 5/01* (2006.01)
*A61B 5/026* (2006.01)
(Continued)

(52) U.S. Cl.
CPC ................ *A61B 5/01* (2013.01); *A61B 5/026* (2013.01); *A61B 5/742* (2013.01); *G01K 1/02* (2013.01); *G01K 13/002* (2013.01); *G06F 1/163* (2013.01); *G06F 1/1626* (2013.01);
*G06F 1/1652* (2013.01); *G06F 1/1684* (2013.01); *G06T 11/206* (2013.01); *G09G 5/02* (2013.01);
(Continued)

(58) Field of Classification Search
CPC ....... G09G 5/02; G06F 1/1626; G06F 1/1684; G06F 1/1652; G06F 1/163; G01K 1/02; G01K 13/002; A61B 5/01; A61B 5/026; A61B 5/742; A61B 2562/0271; A61B 2562/02; A61B 2560/0412; A61B 2562/046; A61B 2562/0233; G06T 11/206
See application file for complete search history.

(56) References Cited

U.S. PATENT DOCUMENTS 3,954,100 A  5/1976 Sem-Jacobsen
4,717,548 A  1/1988 Lee
(Continued)

OTHER PUBLICATIONS

Vertegaal et al.: "Organic User Interfaces," Communications of the ACH, vol. 51, No. 6, pp. 26-30, Jun. 2008.
(Continued)

*Primary Examiner* — Maurice L McDowell, Jr.
(74) *Attorney, Agent, or Firm* — Brundidge & Stanger, P.C.

(57) ABSTRACT

A system for in-place visualization of sensed data is provided. The system includes a formable sheet comprising a display and sensors embedded within the sheet underneath the display. The display will display information relating to sensed data on a portion of the display corresponding to locations of the sensors located underneath the display. As a result, the display displays the information above or directly above the sensors that output data.

19 Claims, 8 Drawing Sheets

(51) Int. Cl.
  *G01K 1/02* (2006.01)
  *G01K 13/00* (2006.01)
  *G06F 1/16* (2006.01)
  *G06T 11/20* (2006.01)
  *G09G 5/02* (2006.01)
  *A61B 5/145* (2006.01)
  *A61B 5/00* (2006.01)

(52) U.S. Cl.
  CPC ......... *A61B 5/14532* (2013.01); *A61B 5/6824* (2013.01); *A61B 2560/0412* (2013.01); *A61B 2562/02* (2013.01); *A61B 2562/0233* (2013.01); *A61B 2562/0271* (2013.01); *A61B 2562/046* (2013.01)

(56) References Cited

U.S. PATENT DOCUMENTS

| | | | |
|---|---|---|---|
| 4,747,413 | A | 5/1988 | Bloch |
| 6,135,949 | A | 10/2000 | Russo et al. |
| 6,640,356 | B1 | 11/2003 | Hans |
| 6,686,843 | B2 | 2/2004 | Felkowitz |
| 7,044,911 | B2 | 5/2006 | Drinan et al. |
| 7,396,157 | B2 | 7/2008 | Liao |
| 8,641,617 | B2 * | 2/2014 | Natarajan .............. A61B 5/026 374/110 |
| 2001/0051767 | A1 * | 12/2001 | Williams ........... A61B 5/14542 600/309 |
| 2002/0000997 | A1 | 1/2002 | Selli et al. |
| 2003/0210146 | A1 | 11/2003 | Tseng |
| 2004/0158156 | A1 | 8/2004 | Schneemeyer et al. |
| 2005/0096513 | A1 | 5/2005 | Ozguz et al. |
| 2005/0141591 | A1 | 6/2005 | Sakano |
| 2005/0174302 | A1 | 8/2005 | Ishii |
| 2005/0245839 | A1 | 11/2005 | Stivoric et al. |
| 2006/0056487 | A1 | 3/2006 | Kuroda et al. |
| 2006/0161074 | A1 | 7/2006 | Liao |
| 2006/0238494 | A1 | 10/2006 | Narayanaswami et al. |
| 2006/0248946 | A1 | 11/2006 | Howell et al. |
| 2007/0125189 | A1 * | 6/2007 | Bossi ................... G01N 27/902 73/865.8 |
| 2007/0279852 | A1 | 12/2007 | Daniel et al. |
| 2008/0004510 | A1 | 1/2008 | Tanzawa et al. |
| 2008/0246726 | A1 | 10/2008 | Gettemy |
| 2008/0312565 | A1 | 12/2008 | Celik-Butler et al. |
| 2009/0030285 | A1 | 1/2009 | Andersen |
| 2009/0126243 | A1 | 5/2009 | Schellingerhout et al. |
| 2009/0219247 | A1 | 9/2009 | Watanabe et al. |
| 2009/0251888 | A1 | 10/2009 | Douglas |
| 2009/0306485 | A1 | 12/2009 | Bell |
| 2010/0002402 | A1 | 1/2010 | Rogers et al. |
| 2010/0029327 | A1 | 2/2010 | Jee |
| 2010/0053207 | A1 | 3/2010 | Cohen et al. |
| 2010/0076276 | A1 | 3/2010 | Gilland |
| 2010/0100160 | A1 | 4/2010 | Edman et al. |

OTHER PUBLICATIONS

Holman et al.: "Organic User Interfaces: Designing Computers in Any Way, Shape, or Form," Communications of the ACH, vol. 51, No. 6, pp. 48-55, Jun. 2008.

* cited by examiner

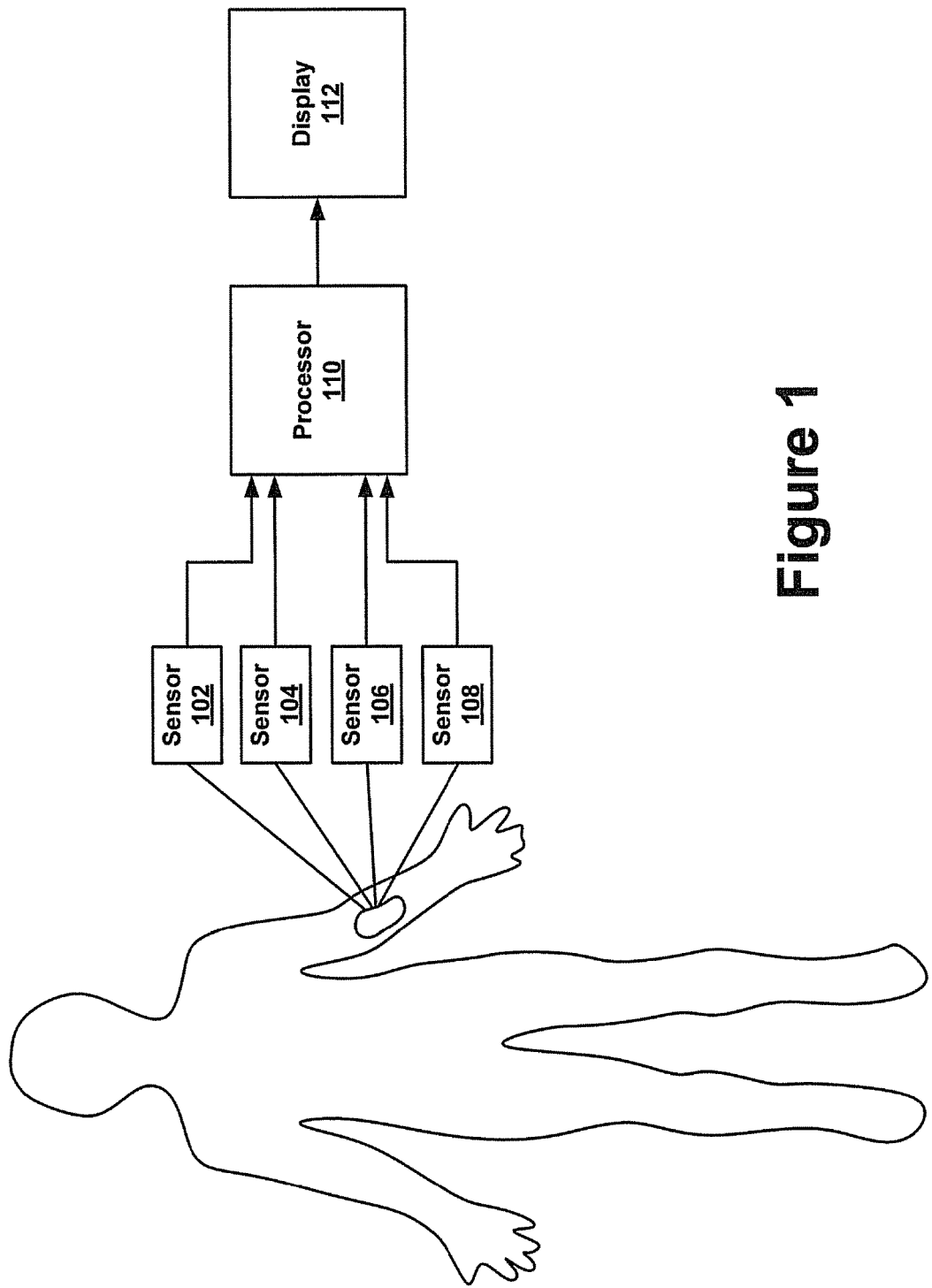

IN-PLACE DISPLAY ON SENSORY DATA

CROSS-REFERENCE TO RELATED APPLICATIONS

The present application is a continuation under 35 U.S.C. § 120 of U.S. application Ser. No. 12/550,199, filed on Aug. 28, 2009, now U.S. Pat. No. 8,641,617, which claims priority under 35 U.S.C. §119(a) to a corresponding patent application filed in India and having application number 766/CHE/2009, filed on Apr. 2, 2009, the entire contents of which are herein incorporated by reference.

BACKGROUND

Many medical procedures intend to achieve a result in the care of a patient by determining, measuring or diagnosing a patient condition or parameter. Other common kinds of procedures may be therapeutic, with an intention of treating, curing or restoring function or structure to a patient.

An example therapeutic procedure includes acupuncture, which attempts to control flow of toxins/blood in the body of a patient. Prior to or during treatment, it may be helpful for a medical practitioner to image the body to study and identify regions that require treatment (e.g., based on low blood flow). However, obtaining real-time feedback regarding effect of the treatment can be difficult.

Many types of medical sensors are available for measuring various health parameters, such as pulse or glucose levels, where a measurement is a scalar value or for measuring distribution of quantities, such as temperature distribution or blood density levels, where a measurement is a scalar field. These measurements are typically stored and analyzed on a desktop computer, and thus, real-time feedback to a medical practitioner may not be available.

Further, visualizing the measurements received from the sensors in real-time can aid the medical practitioner. Similarly, in other fields, such as materials sciences, practitioners could find it to be useful to visualize outputs of sensors that measure physical occurrences in real-time to assist the practitioners in their fields.

SUMMARY

The present application describes a method of in-place visualization of sensed data using a formable member. The formable member includes a flexible display and sensors positioned underneath the flexible display. The method comprises receiving data from the sensors relating to measurements of an object being tested, and displaying information relating to the measurements on portions of the flexible display corresponding to locations of the sensors positioned underneath the display that output the measurements.

In another aspect, a system for in-place visualization of sensed data is provided that includes sensors for making measurements of an object being tested, and a display coupled to the sensors to display information relating to the measurements. The display is coupled to the sensors so that the sensors are positioned underneath the display and so that the sensors are positioned between the object being tested and the display. The display displays information relating to the measurements on portions of the display corresponding to locations of the sensors underneath the display that output the measurements.

In still another aspect, a system for in-place visualization of sensed data is provided that includes a formable member, sensors embedded within the formable member so that the formable member encloses at least a portion of the sensors, and a flexible display positioned within the formable member so that an exposed surface of the formable member includes the flexible display and so that the sensors are positioned underneath the flexible display. The sensors make measurements of an object being tested, and the flexible display is coupled to the sensors to display information relating to the measurements on portions of the flexible display corresponding to locations of the sensors underneath the flexible display that output the measurements.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 illustrates an example system for in-place visualization of sensor data.

DETAILED DESCRIPTION

Figure 2A:
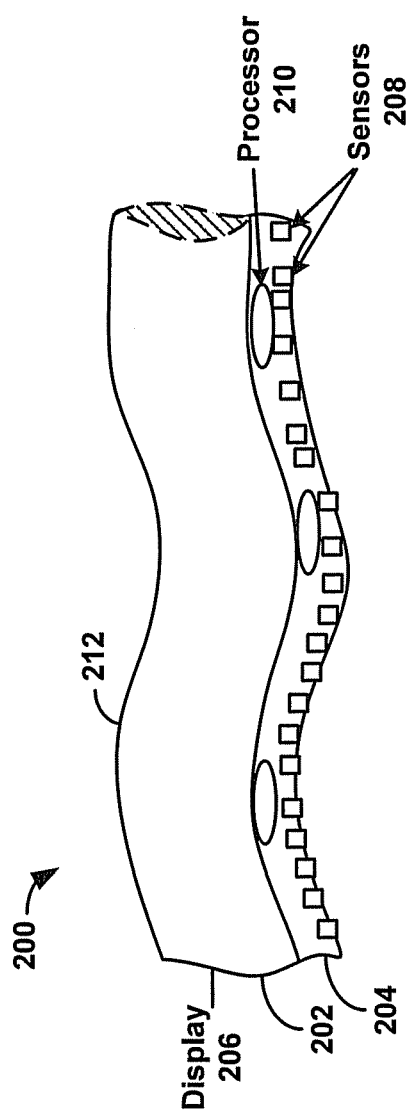
FIG. 2A is a side view of an example illustration of a formable display for in-place visualization of sensor data.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

In the present application, sensors can be used to detect changes in a flow of fluids, for example, and may be embedded within a formable sheet that can be wrapped around a corresponding part of the body. The formable sheet may include embedded processors that process sensed data and an exposed surface of the formable sheet may function as a display device. The formable sheet may then display information relating to sensed data at an area on the sheet corresponding to where the data was sensed by the sensors.

Thus, sensor data can be visualized at a location where the data is gathered. Such in-place visualization may be used to trace effects of radiation on cancerous and healthy cells during an ongoing chemotherapy session, for example. In-place visualization can also be used in domains other than the medical field, such as during non-destructive testing of materials, for example. The formable sheet can be wrapped over or around a material being tested and appropriate sensors embedded in the formable sheet will detect changes to the material being tested that will be illustrated to a user at a location where the changes were detected, for example.

Referring now to the figures, FIG. 1 illustrates a system for in-place visualization of sensor data. The system includes sensors 102, 104, 106 and 108 each coupled to a processor 110, which outputs to a display 112. The sensors 102, 104, 106 and 108 may be placed in an armband, for example, and positioned around a forearm of a person as shown in FIG. 1. In this manner, the sensors 102, 104, 106 and 108 can detect changes in the forearm, such as temperature changes, changes in blood flow, etc.

The sensors 102, 104, 106 and 108 may be any type of sensor appropriate for detecting a change in a material or object that is being tested. In the medical field, for example, the sensors 102, 104, 106 and 108 may be temperature sensors, blood flow sensors, or other sensors that are non-invasive using technology such as near-infrared, ultrasound, etc. In the materials sciences field, for example, the sensors 102, 104, 106 and 108 may be heat sensors, stress sensors, or other types of sensors as applicable.

The sensors 102, 104, 106 and 108 detect a change in the material or object being tested and output measurements or sensed data to the processor 110. The processor 110 may process data and control functionality of the sensors 102, 104, 106 and 108. The processor 110 may be embodied as a processor that accesses internal (or external) memory to execute software functions stored therein. One skilled in the art of computer systems design will understand that the example embodiments are not limited to any particular class or model of processor. The processor may operate according to an operating system, which may be any suitable commercially available embedded or disk-based operating system, or any proprietary operating system. Further, the processor may comprise one or more smaller central processing units, including, for example, a programmable digital signal processing engine or may also be implemented as a single application specific integrated circuit (ASIC) to improve speed and to economize space. In general, it should be understood that the processor 110 could include hardware objects developed using integrated circuit development technologies, or yet via some other methods, or the combination of hardware and software objects that could be ordered, parameterized, and connected in a software environment to implement different functions described herein. Also, the hardware objects could communicate using electrical signals, with states of the signals representing different data.

Furthermore, as mentioned, the processor 110 may include or have access to memory that stores information such as previously transmitted or received signal strengths, for example. The memory may include random access memory (RAM), flash memory or long term storage, such as read only memory (ROM) or magnetic disks, for example.

The processor 110 will receive the outputs from each individual sensor 102, 104, 106 and 108, and will instruct the display 112 to display information at a location corresponding to the sensor that output information. The processor 110 may include a database mapping each sensor to a specific location within the armband, or the output from the sensor may include information indicating a location of the sensor within the armband, so that the processor 110 can instruct the display 112 to display information only for sensors that have output information and only at an area on the display 112 that corresponds to a location of the sensor.

In this manner, the display 112 will display information directly over an area of the material or object being tested at which the change is detected by the sensor, for example. In-place visualization of outputs from the sensors can provide many benefits depending on the specific application. In the medical field, a doctor may be able to monitor blood flow of a patient, and could thus see areas where blood flow may be restricted, for example, based on outputs from the sensors.

FIG. 2A is a side view of an example illustration of a formable display 200 for in-place visualization of sensor data. The formable display 200 may include two layers 202 and 204. One layer 202 includes a display 206. The other layer 204 includes sensors 208 coupled to processors 210. The formable display 200 may also include a power source (not shown), such as a battery to enable the formable display 200 to be portable, for example.

The display 206 may be the type of display that can be constructed to be portable, for example. A thin flexible type of display is one example, however, many other types can work as well. The display 206 may be an electrophoretic display, or another kind of "electronic paper", for example. Examples of commercial electrophoretic displays or other flexible displays include displays constructed from an electrophoretic imaging film manufactured by Electrophoretic ink (E Ink) Corporation, of Cambridge, Mass. Other types of materials may be used for the display as well. For example, Organic Light Emitting Diode (OLED), Light Emitting Polymer (LEP), Organic Electro Luminescence (OEL), and Polymer Light Emitting Diode (PLED) displays may be used. These types of displays may be flexible in nature, and may be referred to as Flexible OLED (FOLED). Example commercial organic displays include displays produced by Sony Corporation of America, of New York, N.Y.

In other examples, the display 206 may include pixels made of electrophoretic ink (E-Ink) and light-emitting polymer technologies resulting in a thin and flexible display that may resemble paper. Textile displays as well are available that include large arrays of LEDs weave into fabrics, which may be used as a form of the display 206, for example.

Using a flexible type of display allows the formable display device 200 to be positioned around materials or objects, and allows for use in more applications. However, the display 206 may also be a conventional type LCD display or other display that is not flexible. Further, the display 206 may include multiple display panels or multiple displays.

The sensors 208 are positioned at various locations within the second layer 204. The sensors 208 may be positioned in arrays, in a grid, or randomly throughout the second layer 204. The sensors 208 are each connected to a processor 210. As shown, the formable device 200 includes many processors 210. Each sensor may only be connected to one processor, and each processor may output to the display 206. Other configurations are possible as well.

Each sensor has a specific location in the second layer 204 of the formable device 200 and has a certain area of coverage for which the sensor can reliably and accurately report a particular aspect that the sensor is observing. The sensor 208 will output to the processor 210, which instructs the display 206 to display information relating to sensed data at a location corresponding to the sensor (discussed more fully below).

As shown, the formable device 200 may include a formable sheet or member 212 that encloses the display 206, the sensors 208, and the processor 210. The display 206 is positioned within the formable member 212 so that an exposed surface of the formable member 212 includes a viewable portion of the display 206. The sensors 208 and the processor 210 are embedded within the formable member 212. The sensors 208 may be fully embedded within the formable member 212, or a portion of the sensors 208 may be exposed as well for contacting a surface of an object being tested, for example. The sensors 208 are positioned underneath the display 206 within the formable member 212 so that the sensors 208 are positioned between the display 206 and an object being tested. Thus, the formable member 212 encloses at least a portion of the display 206 (e.g., a portion of the display 206 may be exposed for viewing), and at least a portion of the sensors 208 (e.g., a portion of the sensors 208 may be exposed for contacting a surface of the object being tested).

Figure 2B:
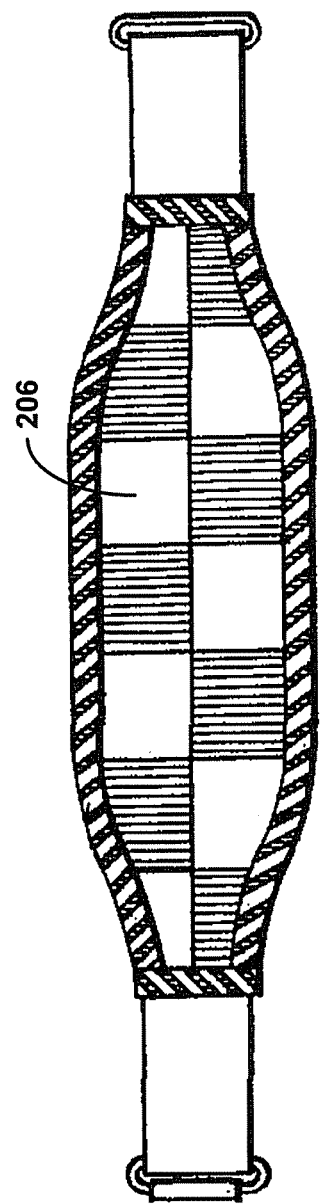
FIG. 2B illustrates a top view of one example of the formable device as an arm band.

The formable device 200 may be used for many applications, and as such, may take many shapes or forms. FIG. 2B illustrates a top view of one example of the formable device as an arm band. The display 206 is illustrated as displaying information in the form of shading or line bars. A location of information displayed on the display 206 indicates a location of the sensed data by the sensors on the material or object being sensed. Thus, if the arm band, as shown in FIG. 2B, were placed around an arm of a person, the information displayed would indicate locations on the arm of the person of sensed data. Conceptually, the arm band formable device would allow a doctor, for example, to have a kind of x-ray view into the arm of the person to visualize locations of distress.

Of course, the formable device 200 may take other forms as well, such as a chest band, a large sheet, a cylindrical form, or any shape and form as needed or as allowed due to a type of display used within the formable device 200. The device could also be rigid, and not formable, for some applications.

Figure 3B:
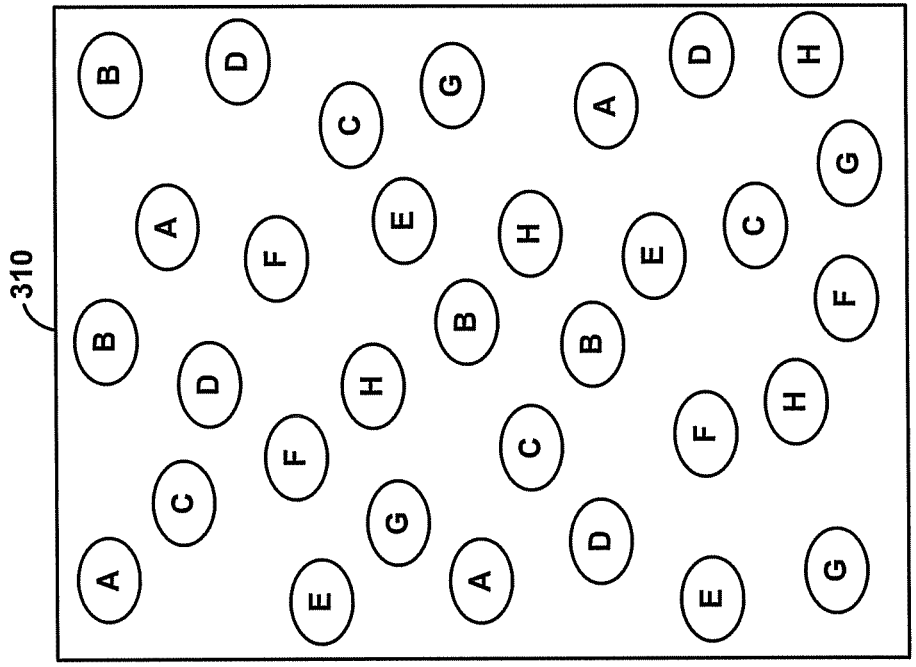
FIGS. 3A-3B are block diagrams illustrating example layouts of sensors in a formable device.
Figure 3A:
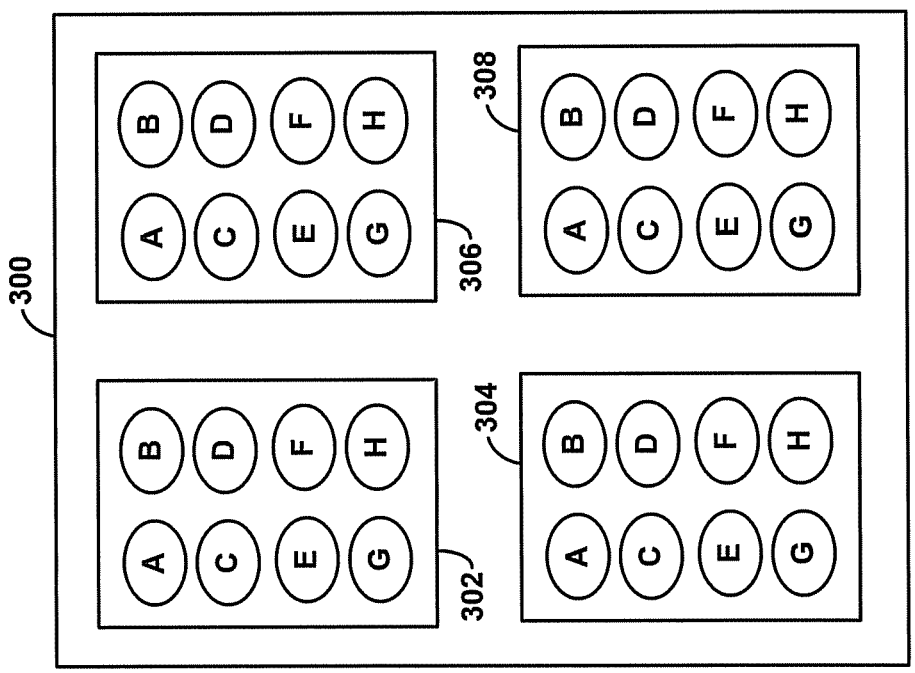

FIG. 3A is a block diagram illustrating an example layout of sensors in a formable device 300. Sensors, such as sensors A-H, may be positioned in linear arrays or rows and columns, and arranged in segments or groupings 302, 304, 306 and 308. Each segment may be coupled to a different processor, for example.

FIG. 3B is a block diagram illustrating another example layout of sensors in a formable device 310. Sensors, such as sensors A-H, may be randomly positioned throughout a layer of the formable device 310. Each corresponding sensor may be coupled to the same processor, so that all A sensors are connected to the same processor, all B sensors are connected to the same processor, all C sensors are connected to the same processor, and so on. Alternatively, sensors in a given area may be connected to the same processor.

FIGS. 3A-3B illustrate example layouts of sensors within one layer of a formable device. The sensors may be positioned in any format as desired, and possibly based on application of the formable device. Further, the formable device may have any number of layers, and any number of sensors positioned within each layer, for example. It may be desirable, for example, to arrange the sensors so that the sensors are distributed evenly throughout the formable device.

Figure 4A:
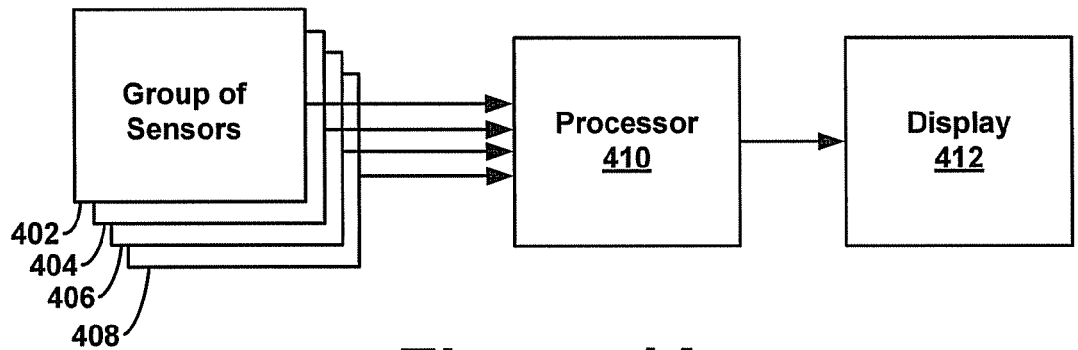
FIGS. 4A-4C are block diagrams illustrating example arrangements of sensors, processors and display in a formable device.
Figure 4B:
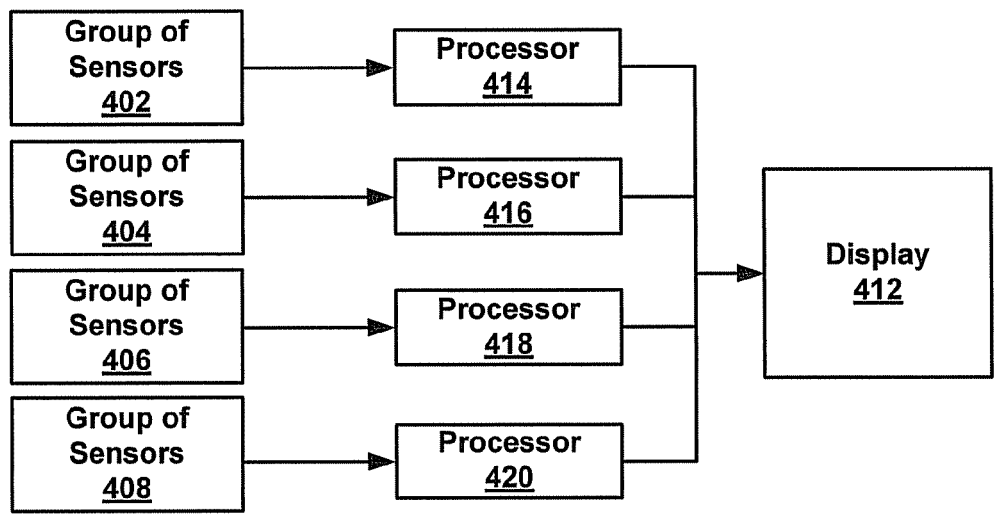
Figure 4C:
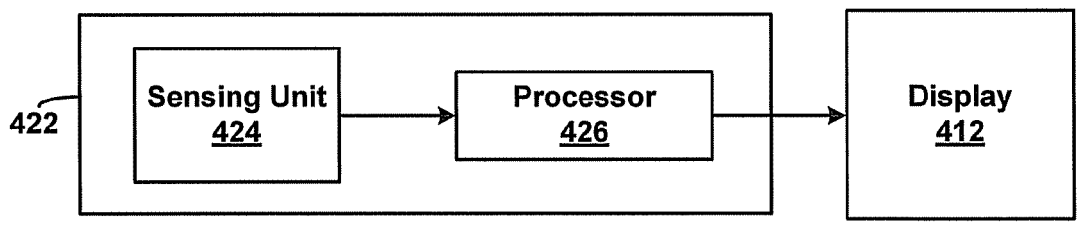

FIG. 4A is a block diagram illustrating one example arrangement of sensors, processors and display in a formable device. Groups of sensors 402, 404, 406 and 408 may each be connected to one processor 410, which outputs to a display 412. Each group of sensors 402, 404, 406 and 408 may include one or more sensors arranged in any type of layout. FIG. 4B is a block diagram illustrating another example arrangement of sensors, processors and display in a formable device. In this example, each group of sensors 402, 404, 406 and 408 is connected to a processor, such as processors 414, 416, 418 and 420, respectively. Each processor 414, 416, 418 and 420 outputs to the display 412. FIG. 4C is a block diagram illustrating another example arrangement of sensors, processors and display in a formable device. In this example, each sensor, such as sensor 422, may include a sensing unit 424 that outputs to an interior processor 426. The sensor 422 may then output directly to the display 412.

FIGS. 4A-4C are example arrangements only, and other arrangements may be used instead depending on types of sensors, types of processors and types of displays used in the formable device. Of course, although not shown, more than one display may be included as well, or the display may be provided in segments, and processors or sensors may only output to a given segment, for example.

Figure 5:
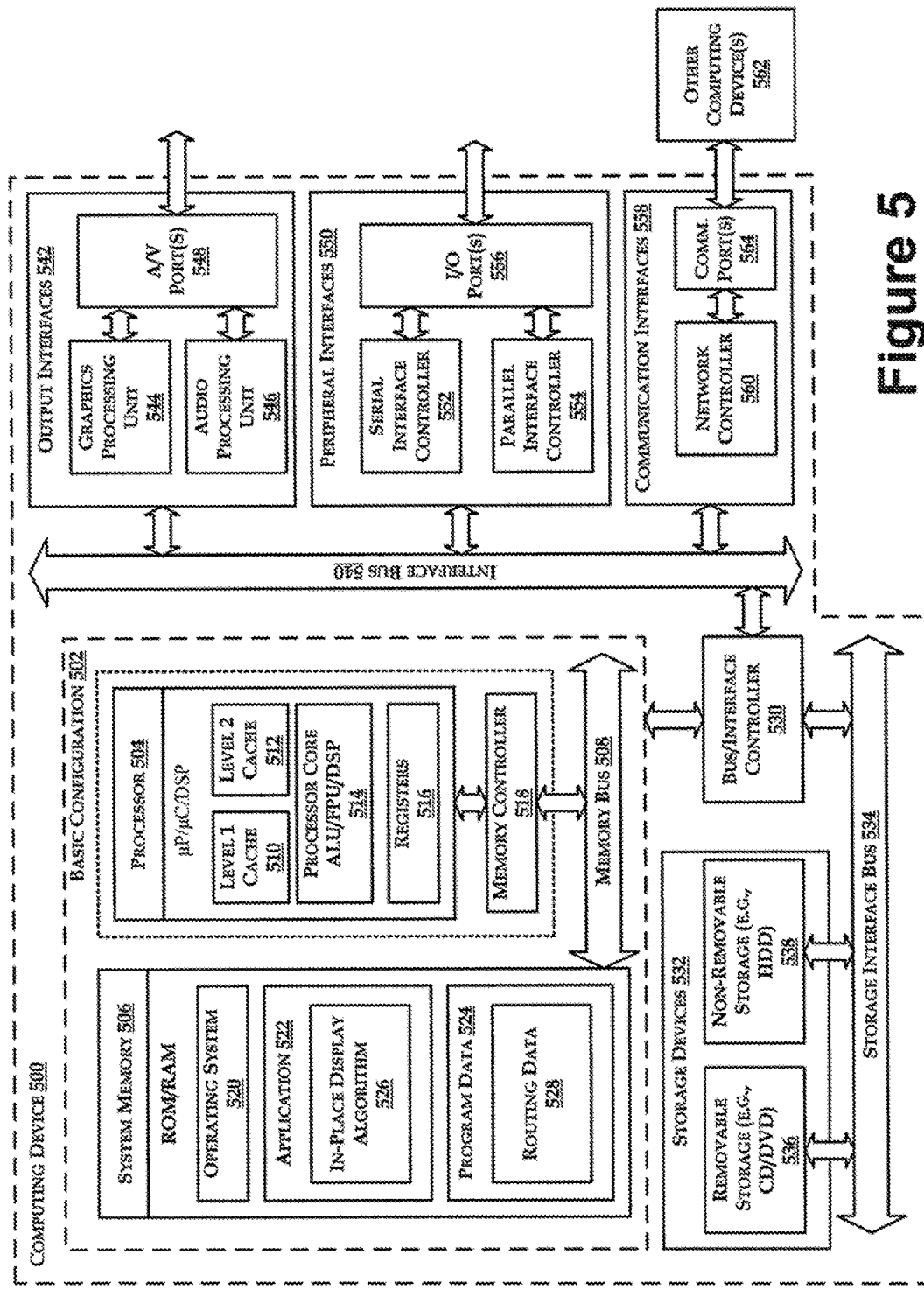
FIG. 5 is a block diagram illustrating an example computing device that is arranged as a formable device.

FIG. 5 is a block diagram illustrating an example computing device 500 that is arranged as a formable device. In a basic configuration 502, the computing device 500 typically includes one or more processors 504 and system memory 506. A memory bus 508 can be used for communicating between the processor 504 and the system memory 506.

Depending on a desired configuration, the processor 504 can be of any type including but not limited to a microprocessor (μP), a microcontroller (μC), a digital signal processor (DSP), or any combination thereof. The processor 504 can include one more levels of caching, such as a level one cache 510 and a level two cache 512, a processor core 514, and registers 516. The processor core 514 can include an arithmetic logic unit (ALU), a floating point unit (FPU), a digital signal processing core (DSP Core), or any combination thereof. A memory controller 518 can also be used with the processor 504, or in some implementations the memory controller 518 can be an internal part of the processor 504, for example.

Depending on a desired configuration, the system memory 506 can be of any type including but not limited to volatile memory (such as RAM), non-volatile memory (such as ROM, flash memory, etc.) or any combination thereof. The system memory 506 typically includes an operating system 520, one or more applications 522, and program data 524. The application 522 includes, for example, an in-place visualization and display of sensed data processing algorithm 526 that is arranged to receive sensed data and inform a display how and where to display the data (as more fully described below with reference to FIG. 7). The program data 524 includes routing data 528 that is useful for routing sensed data to the display, as will be further described below. In some example embodiments, the application 522 can be arranged to operate with the program data 524 on the operating system 520 such that sensed data is display on portions of a display corresponding to location of the sensors positioned underneath the display that sensed the data, for example. This described basic configuration 502 is illustrated in FIG. 5 by those components within dashed line 502.

The computing device 500 can have additional features or functionality, and additional interfaces to facilitate communications between the basic configuration 502 and any required devices and interfaces. For example, a bus/interface controller 530 can be used to facilitate communications between the basic configuration 502 and one or more data storage devices 532 via a storage interface bus 534. The data storage devices 532 can be removable storage devices 536, non-removable storage devices 538, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and non-volatile, removable and non-removable media implemented in any method or technology for storage of information, such as computer readable instructions, data structures, program modules, or other data.

The system memory 506, removable storage 536 and non-removable storage 538 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by the computing device 500. Any such computer storage media can be part of the computing device 500.

The computing device 500 can also include an interface bus 540 for facilitating communication from various interface devices (e.g., output interfaces, peripheral interfaces, and communication interfaces) to the basic configuration 502 via the bus/interface controller 530. Example output interfaces 542 include a graphics processing unit 544 and an audio processing unit 546, which can be configured to communicate to various external devices such as a display or speakers via one or more audio/visual (A/V) ports 548. Example peripheral interfaces 550 include a serial interface controller 552 or a parallel interface controller 554, which can be configured to communicate with external devices such as input devices (e.g., keyboard, mouse, pen, voice input device, touch input device, etc.) or other peripheral devices (e.g., printer, scanner, etc.) via one or more input/output (I/O) ports 556. An example communication interface 558 includes a network controller 560, which can be arranged to facilitate communications with one or more other computing devices 562 over a network communication via one or more communication ports 564. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media as used herein can include both storage media and communication media.

The computing device 500 can be implemented as a portion of a small-form factor portable (or mobile) electronic device.

Figure 6:
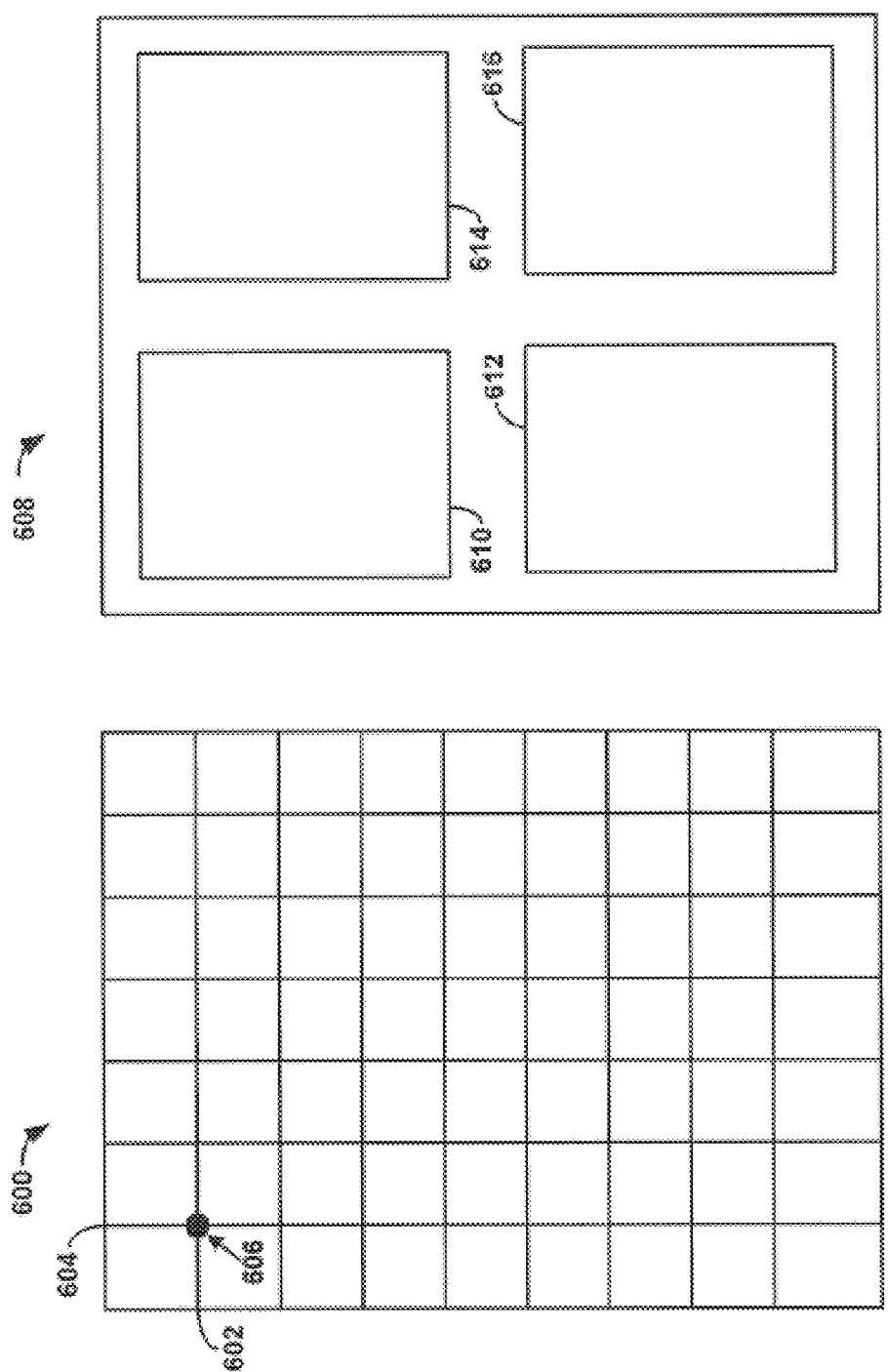
FIGS. 6A-6B are conceptual diagrams illustrating example layouts of a display.

FIG. 6A is a conceptual diagram illustrating a layout of a display 600. The display 600 includes pixels arranged in rows and columns, such as row 602 and column 604. To address a particular pixel, a proper row is switched on, and then a charge is sent down a corresponding column. Each row and column may be an anode and cathode and by sending a voltage down corresponding rows and columns, a pixel can receive a charge. For example, a pixel at intersection point 606 may receive a charge through row 602 and column 604. A capacitor at the intersection point may be able to hold the charge until a next refresh cycle. An intensity level of the charge can affect illumination of the pixel, for example. Thus, the display 600 may be arranged such that intersection of two electrodes in any type of gridded structure, where one electrode performs as an anode and a crossing electrode performs as a cathode, illuminates a pixel. The anode layer may overlay a thin film transistor (TFT) array that forms a matrix, which determines which pixels are turned on to form an image, for example. This type of layout may be beneficial if an OLED or formable display is used.

FIG. 6B is a diagram illustrating another layout of a display 608. The display 608 may include segments 610, 612, 614 and 616. Each segment 610, 612, 614 and 616 may be the same type of display or different types of displays. Using this layout, the segments 610, 612, 614 and 616 do not need to be formable themselves, and the device may still operate as a formable device is the underlying structure of the device is formable, for example. Thus, the segments 610, 612, 614 and 616 may be rigid liquid crystal displays (LCDs) or other types, for example, and material between the displays 610, 612, 614 and 616 may be flexible.

Figure 7:
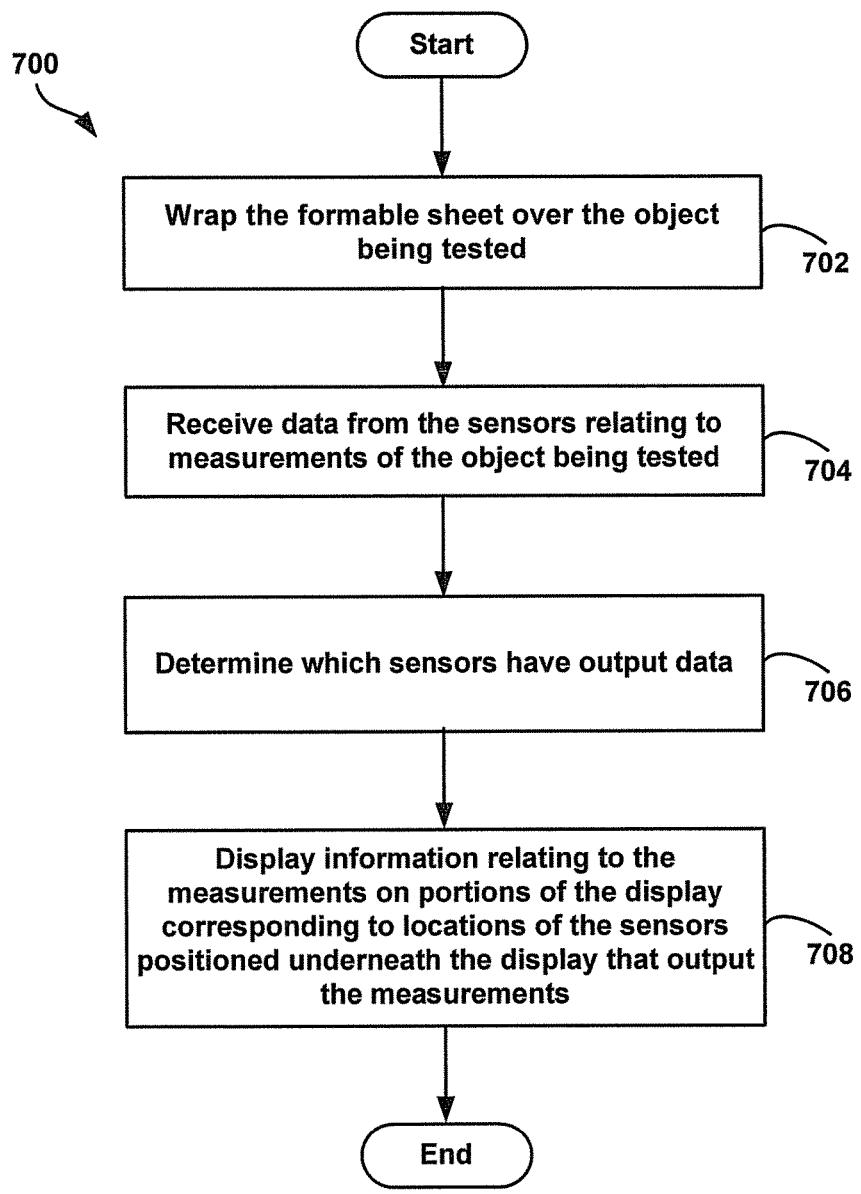
FIG. 7 is a flowchart depicting example steps of a method for in-place visualization and display of sensed data.

FIG. 7 is a flowchart depicting example steps of a method 700 for in-place visualization and display of sensed data. It should be understood that the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

A formable device, such as that described in FIG. 2 or the computing device described in FIG. 5, may be used to perform the method illustrated in FIG. 7, for example. Initially, a formable sheet can be wrapped over an object being tested, as shown at block 702. Sensors within the formable sheet will record measurements of an object being tested, and a processor will receive data from the sensors relating to the measurements, as shown at block 704. The processor will determine which sensors have output data, either based on a port of the processor that received the data (e.g., each sensor may output data to a specific port of the processor) or based on information within the data, as shown at block 706.

The processor will then instruct the display to display information relating to the measurements on portions of the display corresponding to locations of the sensors positioned underneath the display that output the measurements, as shown at block 708. The information relating to the measurements will be displayed on portions of the display located above a given sensor that output a given measurement. In this manner, a user can view an output of the sensor in place, as if the sensor itself includes a display, for example.

The processor may instruct the display or send signals to the display using standard video graphics array (VGA) or digital video interface (DVI) signaling. A wired connection between the processor and the display is used to address individual pixels on the display to instruct specific regions of the display to switch on/off, for example. The processor may map portions of the display to correspond to outputs of specific sensors based on a location of the sensors underneath the display. In this manner, for example, the display can display outputs of sensors above or directly above the sensors that provided the outputs.

An exposed surface of the formable sheet includes the display, and thus, a user will be able to view the display and read the information relating to the measurements. The information may include a combination of patterns, glyphs, textual information, or other as applicable to an application of the device and the object being tested. Information may be displayed using multiple colors as well.

Figure 8A:
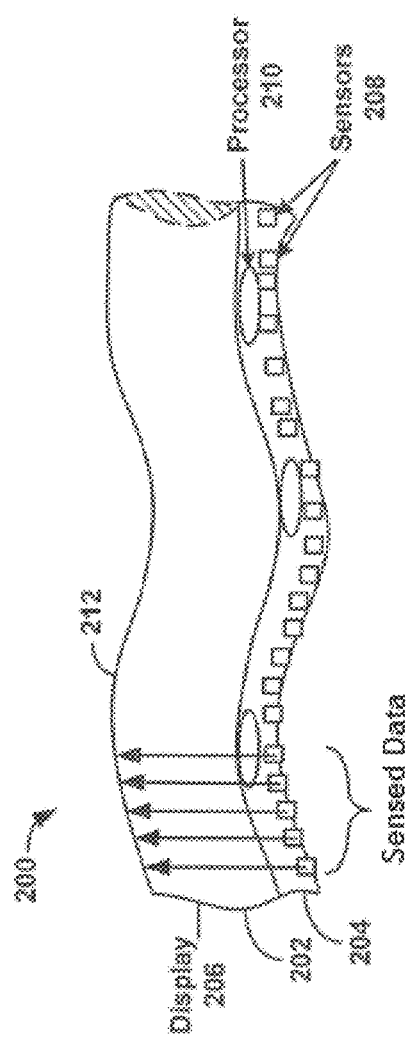
FIG. 8A illustrates an example side view of the formable display of FIG. 2A.
Figure 8B:
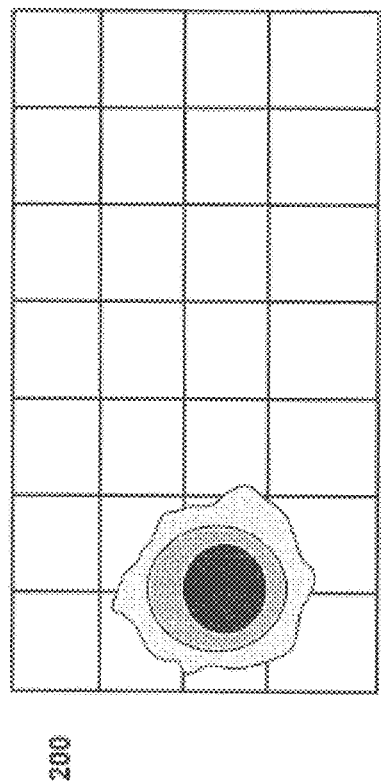
FIG. 8B is an example illustration of a top view of the formable display of FIG. 2A.

FIG. 8A illustrates a side view of the formable display 200 of FIG. 2A, and FIG. 8B is an example illustration of a top view of the display 206. FIGS. 8A-8B illustrate one example conceptual operation of the formable display 200. As shown in FIG. 8A, only the five leftmost sensors sense data in this example. Thus, the display 206 will display information relating to the sensed data on a portion of the display corresponding to locations of the five leftmost sensors located underneath the display 206. As a result, the display 206 displays the information above or directly above the five leftmost sensors, as shown in FIG. 8B. In this manner, a user will directly know where data was sensed, for example, on the object being tested.

Further, as shown in FIG. 8B, the information may be displayed in various shades of color or various colors, and various shapes, depending on the type of sensor and the data being sensed. As one example, the sensors in FIG. 8A may be temperature sensors, and the display shown in FIG. 8B indicates temperatures of the object being tested such that a darker shade represents a higher temperature. Further away from a center of the sensed location, temperatures of the object being tested may decrease, as shown by the lighter shades of color, for example.

The formable device of the present application may also output to a computer for additional processing of the information as well.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

It should be further understood that this and other arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

The invention claimed is:

1. A method to present sensor data, comprising:
sensing, by a sensor, a parameter that relates to an object being tested;
generating, by the sensor, a measurement based on the sensed parameter; and
in response to generation of the measurement by the sensor, displaying, on a flexible display coupled to the sensor, information that relates to the measurement on a portion of the flexible display corresponding to a location above the sensor,
wherein the displaying on the flexible display includes displaying a real-time pictorial gradient of the measurement that includes a first shade of a color to represent a first gradient of the measurement and a second shade of the color, different in shade than the first shade, to represent a second gradient of the measurement, wherein the second gradient includes a different value relative to a value of the first gradient.

2. The method of claim 1, wherein the second shade is different in shade than the first shade by being lighter in shade than the first shade.

3. The method of claim 1, wherein the different value relative to the value of the first gradient includes a decreased value relative to the value of the first gradient.

4. The method of claim 1, wherein the sensing the parameter includes at least one of sensing a change in temperature or sensing a change in blood flow of the object being tested.

5. The method of claim 1, wherein the sensor includes a first sensor, the parameter includes a first parameter, and the measurement includes a first measurement, the method further comprising:
sensing, by a second sensor, a second parameter that relates to the object being tested; and
generating, by the second sensor, a second measurement based on the second sensed parameter, the second measurement corresponding to a location, below the second sensor, that is different from a location below the first sensor.

6. The method of claim 5, wherein the real-time pictorial gradient includes a first real-time pictorial gradient, and wherein the displaying on the flexible display further includes displaying a second real-time pictorial gradient of the first and second measurements.

7. The method of claim 1, wherein the sensor is in contact with the object being tested.

8. A non-transitory computer-readable medium that includes executable instructions stored thereon that, in response to execution, cause a processor to perform operations, comprising:
control a sensor to sense a parameter that relates to an object being tested;
control generation of a measurement based on the parameter sensed by the sensor; and
control a flexible display, coupled to the sensor, to display information that relates to the measurement on a portion of the flexible display corresponding to a location above the sensor,
wherein the displayed information includes a real-time pictorial gradient of the measurement that includes a first shade of a color to represent a first gradient of the measurement and a second shade of the color, different in shade than the first shade, to represent a second gradient of the measurement, wherein the second shade includes a different value relative to a value of the first gradient.

9. The non-transitory computer-readable medium of claim 8, wherein the second shade is different in shade than the first shade by being lighter in shade than the first shade.

10. The non-transitory computer-readable medium of claim 8, wherein the different value relative to the value of the first gradient includes a decreased value relative to the value of the first gradient.

11. The non-transitory computer-readable medium of claim 8, wherein the operations to control the sensor to sense the parameter include operations to control the sensor to sense at least one of a change in temperature or a change in blood flow of the object being tested.

12. The non-transitory computer-readable medium of claim 8,
wherein the sensor includes a first sensor, the parameter includes a first parameter, and the measurement includes a first measurement, and
wherein the executable instructions, in response to execution, cause the processor to perform further operations, comprising:
control a second sensor to sense a second parameter that relates to the object being tested, and
control generation of a second measurement based on the second parameter sensed by the second sensor, the second measurement corresponding to a location, below the second sensor, that is different from a location below the first sensor.

13. The non-transitory computer-readable medium of claim 12, wherein the real-time pictorial gradient includes a first real-time pictorial gradient, and wherein the executable instructions, in response to execution, cause the processor to perform further operations, comprising:

control the flexible display to display a second real-time pictorial gradient of the first and second measurement.

14. An apparatus, comprising:

a flexible display that includes a viewable portion; and at least one sensor positioned underneath the flexible display and configured to sense at least one parameter of an object being tested, wherein a first location of the at least one sensor corresponds to a second location within the viewable portion that lies at least partially directly above the first location, wherein the flexible display is configured to display information in the second location within the viewable portion that pertains to the at least one parameter that is sensed by the at least one sensor, wherein the displayed information includes a real-time pictorial gradient of a measurement, wherein the at least one parameter includes a first parameter and a second parameter, the measurement includes a first measurement, and the real-time pictorial gradient includes a first real-time pictorial gradient, wherein the at least one sensor is further configured to:
sense the second parameter of the object being tested, and generate a second measurement based on the second sensed parameter, the second measurement corresponding to a location different from the first location, and wherein the flexible display is configured to further display a second real-time pictorial gradient of the first and second measurements.

15. The apparatus of claim 14, wherein the at least one sensor is further configured to generate the first measurement based on the sensed at least one parameter.

16. The apparatus of claim 15, wherein the real-time pictorial gradient of the measurement includes a first shade of a color to represent a first gradient of the first measurement and a second shade of the color, different in shade than the first shade, to represent a second gradient of the first measurement, and wherein the second gradient includes a different value relative to a value of the first gradient.

17. The apparatus of claim 16, wherein the second shade is different in shade than the first shade by being lighter in shade than the first shade.

18. The apparatus of claim 16, wherein the different value relative to the value of the first gradient includes a decreased value relative to the value of the first gradient.

19. The apparatus of claim 14, wherein the at least one parameter includes at least one of a change in temperature or a change in blood flow of the object being tested.

* * * * *